United States Patent
Beso et al.

(10) Patent No.: US 9,622,976 B2
(45) Date of Patent: Apr. 18, 2017

(54) PHARMACEUTICAL COMPOSITION

(71) Applicant: LEK PHARMACEUTICALS D.D., Ljubljana (SI)

(72) Inventors: Adnan Beso, Novo mesto (SI); Igor Legen, Grosuplje (SI); Sebastjan Reven, Jecenice (SI)

(73) Assignee: Lek Pharmaceuticals d.d. (SI)

( * ) Notice: Subject to any disclaimer, the term of this patent is extended or adjusted under 35 U.S.C. 154(b) by 0 days.

(21) Appl. No.: 14/158,405

(22) Filed: Jan. 17, 2014

(65) Prior Publication Data

US 2014/0134247 A1 May 15, 2014

Related U.S. Application Data

(63) Continuation of application No. 12/304,942, filed as application No. PCT/EP2007/005248 on Jun. 14, 2007, now Pat. No. 8,685,452.

(30) Foreign Application Priority Data

Jun. 16, 2006 (EP) .................................. 06012381

(51) Int. Cl.

| | |
|---|---|
| *A61K 9/20* | (2006.01) |
| *A61K 9/24* | (2006.01) |
| *A61K 9/28* | (2006.01) |
| *A61K 31/4184* | (2006.01) |
| *A61K 31/5415* | (2006.01) |
| *A61K 9/16* | (2006.01) |
| *A61K 31/549* | (2006.01) |
| *A61K 9/50* | (2006.01) |

(52) U.S. Cl.
CPC ............ *A61K 9/2027* (2013.01); *A61K 9/167* (2013.01); *A61K 9/209* (2013.01); *A61K 9/282* (2013.01); *A61K 9/284* (2013.01); *A61K 9/2866* (2013.01); *A61K 31/4184* (2013.01); *A61K 31/549* (2013.01); *A61K 31/5415* (2013.01); *A61K 9/2077* (2013.01); *A61K 9/5084* (2013.01)

(58) Field of Classification Search
None
See application file for complete search history.

(56) References Cited

U.S. PATENT DOCUMENTS

| | | | |
|---|---|---|---|
| 4,444,769 A | 4/1984 | Blume et al. | |
| 4,547,498 A | 10/1985 | Blume et al. | |
| 6,479,551 B1 | 11/2002 | Plachetka et al. | |
| 8,685,942 B2 * | 4/2014 | Gross et al. | .................... 514/53 |
| 2002/0052367 A1 | 5/2002 | Heller | |
| 2004/0110813 A1 | 6/2004 | Nakatani et al. | |
| 2004/0198789 A1 | 10/2004 | Leonardi et al. | |
| 2005/0004107 A1 * | 1/2005 | Kohlrausch | ................ 514/223.5 |
| 2005/0013863 A1 | 1/2005 | Lim et al. | |
| 2005/0020671 A1 * | 1/2005 | Fernandez Ibanez et al. | ............................ 514/471 |
| 2005/0089575 A1 | 4/2005 | Friedl et al. | |
| 2005/0143435 A1 | 6/2005 | Baum et al. | |
| 2005/0186274 A1 | 8/2005 | Kohlrausch | |

FOREIGN PATENT DOCUMENTS

| | | | |
|---|---|---|---|
| EP | 0 747 050 A1 | 12/1996 | |
| WO | WO 03/059327 * | 7/2003 | ............... A61K 9/20 |
| WO | WO 03/059327 A1 | 7/2003 | |
| WO | WO 03/059388 A1 | 7/2003 | |
| WO | WO 2004/028505 A1 | 4/2004 | |
| WO | WO 2004/096215 A1 | 11/2004 | |
| WO | WO 2005/039639 A2 | 5/2005 | |

OTHER PUBLICATIONS

Breuer et al. Glossary of terms related to pharmaceutics, IUPAC-81(5), 2009, pp. 971 and 977.
Rowe et al., APhA Handbook of Pharmaceutical Excipients, 2003, pp. 508-513.
Stuart C. Porter., "Coating of Pharmaceutical Dosage Forms", Remington, The Science and Practice of Pharmacy 20 Ed., (46), 2000, p. 894.

* cited by examiner

*Primary Examiner* — Brian Gulledge
(74) *Attorney, Agent, or Firm* — Luedeka Neely Group, P.C.

(57) ABSTRACT

A stable formulation of telmisartan and hydrochlorothiazide having both substances in separate units is prepared, exhibiting exceptional stability when subjecting to stress conditions.

7 Claims, No Drawings

PHARMACEUTICAL COMPOSITION

CROSS-REFERENCE TO RELATED APPLICATION

This application is a Continuation of application Ser. No. 12/304,942, having a 371 date of Feb. 20, 2009, which is a Section 371 national phase entry of PCT International Application No. PCT/EP2007/005248, filed Jun. 14, 2007, which claims priority to European Patent Application No. 06012381.7 filed Jun. 16, 2006, the entire specification claims and drawings of which are incorporated herein by reference.

FIELD OF THE INVENTION

Present invention from the field of pharmaceutics discloses pharmaceutical composition comprising a combination of two active pharmaceutical ingredients, of which is one alkaline, or in alkaline environment and the other is labile in alkaline environment, and specifically relates to telmisartan or its alkali salt and hydrochlorothiazide.

BACKGROUND OF THE INVENTION 6-chloro-3,4-dihydro-2H-1,2,4-benzotiadiazine-7-sulfonamide-1,1-dioxide known as hydrochlorothiazide and abbreviated HCT has been long used as an active pharmaceutical ingredient to treat hypertension. Telmisartan in acidic form or as an alkali, preferably sodium, salt is another active pharmaceutical ingredient and may be used as an angiotenzin II antagonist. Chemically telmisartan is a 2-[4-[[4-methyl-6-(1-methylbenzoimidazol-2-yl)-2-propyl-benzoimidazol-1-yl]methyl]phenyl]benzoic acid. Telmisartan itself is at neutral pH poorly soluble. That is, it does not dissolve more than 2 µg per ml of pH 6.8 phosphate buffer. In order to increase its bioavailability, it is normally administered as an alkaline salt, such as sodium salt or incorporated into a composition which itself provides for an alkaline pH. It is advantageous to administer both drugs concomitantly or even more to manufacture a composition comprising both to treat hypertension. Such composition is known from WO 03/059327, however specific technology was used therein to prevent the degradation of hydrochlorothiazide which inevitably occurs when this substance is exposed to alkaline media. The main degradation product of hydrochlorothiazide is 4-amino-6-chloro-1,3-benzenedisulfonamide (DSA).

By providing said hydrochlorothiazide and another alkaline active substance, in separate units, a stable pharmaceutical composition could be prepared. Separating hydrochlorothiazide, which degrades under alkaline conditions from another alkaline active substance requires special pharmaceutical composition manufacturing machinery. Additional difficulty represents the fact, that both active substances need to be released from the composition substantially concomitantly.

DISCLOSURE OF THE INVENTION

In an aspect the invention provides a pharmaceutical composition for immediate release comprising as an active substance 6-chloro-3,4-dihydro-2H-1,2,4-benzotiadiazine-7-sulfonamide-1,1-dioxide together with one or more alkaline active or inactive ingredients (excipients).

Generally the invention is pharmaceutical composition, preferably for oral administration, comprising at least one first unit, selected from granules, pellets, or tablet cores; wherein said first unit comprises first active pharmaceutical ingredient together with pharmaceutically acceptable excipients and a) at least one second unit, selected from granules, pellets, or tablet cores, where said second unit comprises a second active pharmaceutical ingredient, together with pharmaceutically acceptable excipients, wherein said at least one first and at least one second unit are together with a suitable carrier compressed into a tablet where said units are substantially evenly distributed throughout the tablet; or b) at least one coating comprising a second active pharmaceutical ingredient applied onto said first unit, where either first or second active pharmaceutical ingredients is 6-chloro-3,4-dihydro-2H-1,2,4-benzotiadiazine-7-sulfonamide-1,1-dioxide and unit comprising the other active pharmaceutical ingredient is characterized in that said unit alone imparts pH above 8 to the 1% by weight aqueous solution or dispersion of said other unit, where said unit preferably comprises 2-[4-[[4-methyl-6-(1-methylbenzoimidazol-2-yl)-2-propyl-benzoimidazol-1-yl]methyl]phenyl]benzoic acid or a salt thereof as the other active pharmaceutical ingredient.

Specifically the invention is a pharmaceutical composition comprising at least one first unit, selected from granules, pellets, or tablet cores; wherein said first unit comprises 2-[4-[[4-methyl-6-(1-methylbenzoimidazol-2-yl)-2-propyl-benzoimidazol-1-yl]methyl]phenyl]benzoic acid or a salt thereof together with pharmaceutically acceptable excipients and at least one second unit, selected from granules, pellets, or tablet cores, where said second unit comprises 6-chloro-3,4-dihydro-2H-1,2,4-benzotiadiazine-7-sulfonamide-1,1-dioxide, together with pharmaceutically acceptable excipients, wherein said at least one first and at least one second unit are together with a suitable carrier compressed into tablet; or at least one coating comprising 6-chloro-3,4-dihydro-2H-1,2,4-benzotiadiazine-7-sulfonamide-1,1-dioxide applied onto said first unit.

In a more specific aspects said first and second unit are selected from more than one granule or more then one pellet or more than one tablet core. In another more specific aspects an optional coating is applied to said first or said second unit, wherein said coating comprises a polymer appropriate for conventional film coating.

In another aspect the invention is a pharmaceutical composition comprising at least one first unit, preferably selected from granules, pellets, and small tablet cores, comprising 2-[4-[[4-methyl-6-(1-methylbenzoimidazol-2-yl)-2-propyl-benzoimidazol-1-yl]methyl]phenyl]benzoic acid or a salt thereof, with optional coating applied to said first unit, wherein said coating comprises a polymer appropriate for conventional film coating; and at least one second unit, preferably selected from granules, pellets, and mixture of powders comprising 6-chloro-3,4-dihydro-2H-1,2,4-benzotiadiazine-7-sulfonamide-1,1-dioxide, wherein said at least one first and at least one second unit are together with a suitable carrier compressed into a pharmaceutical composition, or filled into a capsule.

In another more specific aspects the pharmaceutical composition is a tablet, preferably a matrix tablet.

In yet another more specific aspects the amount of said carrier is from 10 to 50% by weight of the composition, preferably wherein said carrier is selected from the group consisting of cellulose ether, acrylic polymer, polyvinylpyrrolidone, polyethylene glycol. Preferably the weight ratios of said first units, second units and carrier may be 1-5:1-3:1-2.

In yet another aspect the invention is a pharmaceutical composition comprising at least one first unit, preferably selected from granules, pellets, and tablet cores, comprising 2-[4-[[4-methyl-6-(1-methylbenzoimidazol-2-yl)-2-propyl-benzoimidazol-1-yl]methyl]phenyl]benzoic acid or a salt thereof, with optional coating applied to said unit, wherein said coating comprises a polymer appropriate for conventional film coating; and a coating comprising 6-chloro-3,4-dihydro-2H-1,2,4-benzotiadiazine-7-sulfonamide-1,1-dioxide applied onto said first unit, preferably said first unit is a tablet core.

Another aspect of the invention is the pharmaceutical composition made of first and second units as described above, wherein one or more second units are selected from granules, pellets or tablet cores and those said second units comprise 3 to 15% hydrochlorothiazide, 10 to 95% of one or more soluble diluents, preferably lactose, 1 to 10% of substance with suspension stabilizing properties, preferably colloidal silicon dioxide, 5 to 15% of binder, preferably polyvinylpyrrolidone and optionally up to 10% of an acidifying agent, preferably citric acid by weight relative to the weight of said second cores, preferably wherein said second units represent from 5 to 80, preferably 10 to 60%, more preferably 15 to 33% by weight of said pharmaceutical composition.

Aspect of the invention is also is the pharmaceutical composition made of first and second units as described above, wherein one or more first units comprise 1 to 50% telmisartan; 1 to 50% binder, 1 to 80% soluble diluent, and 1 to 12% alkalizing agent by weight relative to the weight of the said first units, preferably wherein said first units represent from 10 to 95%, preferably 25 to 95%, more preferably 33 to 66% by weight of said pharmaceutical composition preferably wherein said first units are prepared by first preparing a granulate, preferably by wet granulation, and compressing said granulate with one or more additional diluents, binders and lubricants into tablets; or compressed into tablets by dry compression or formulated into pellets by extrusion and spheronisation.

An important aspect of the invention is a pharmaceutical composition comprising a first unit which is a tablet core that comprises 1 to 40% telmisartan; 1 to 40% binder, 1 to 50% soluble diluent, and 1 to 10% alkalizing agent by weight relative to the weight of the composition; and a coating that comprises 10 to 40% hydrochlorothiazide and 10 to 40% colloidal silicon dioxide, 20 to 60% polyvinylpyrrolidone, 5 to 50% plasticizer and optionally up to 10% acidifying agent by weight relative to the weight of coating and the coating constitutes from about 3 to about 25% by weight of the finished composition.

In an aspect a separating coating which constitutes from about 0.1 to about 10% by weight of the finished composition is applied onto one or more said first unit, preferably comprising one or more polymers selected from cellulose derivative, polyethileneglycols and polyvinylpyrrolidone.

Due to its stabilizing properties the use of polyvinylpyrrolidone as a binder in manufacturing of pharmaceutical composition comprising telmisartan in one or more first units, selected from granules, pellets, aglomerates or tablets, and hydrochlorothiazide in one or more second units, selected from granules, pellets, aglomerates or tablets or in a coating applied onto said first units, characterized in that polyvinylpyrrolidone is incorporated into said second units or said coating is an important aspect of the invention, preferably wherein polyvinylpyrrolidone is incorporated into said second units or said coating in ratio above 0.5, preferably above 1 by weight to the hydrochlorothiazide.

Manufacturing aspects of the invention represent a process for manufacturing a pharmaceutical composition characterized in that the first units are manufactured comprising 2-[4-[[4-methyl-6-(1-methylbenzoimidazol-2-yl)-2-propyl-benzoimidazol-1-yl]methyl]phenyl]benzoic acid or its salt; onto those units an optional separating coating is applied; and a coating comprising 6-chloro-3,4-dihydro-2H-1,2,4-benzotiadiazine-7-sulfonamide-1,1-dioxide is applied thereto; or second units are manufactured comprising 6-chloro-3,4-dihydro-2H-1,2,4-benzotiadiazine-7-sulfonamide-1,1-dioxide; and at least one said first unit and at least one second unit are filled into capsule or compressed together with a suitable carrier into tablet.

Another manufacturing aspects is process for manufacturing a pharmaceutical composition comprising following steps: preparing a tablet core comprising 2-[4-[[4-methyl-6-(1-methylbenzoimidazol-2-yl)-2-propyl-benzoimidazol-1-yl]methyl]phenyl]benzoic acid or its salt; optionally applying an optional coating thereto; and applying a coating comprising 6-chloro-3,4-dihydro-2H-1,2,4-benzotiadiazine-7-sulfonamide-1,1-dioxide.

The tablet core is preferably prepared by a process comprising: wet granulation of blend comprising by weight relative to the weight of tablet core 5 to 33% of 2-[4-[[4-methyl-6-(1-methylbenzoimidazol-2-yl)-2-propyl-benzoimidazol-1-yl]methyl]phenyl]benzoic acid or its salt; up to 10% of an alkalizing agent, preferably an alkali or earth alkali hydroxide or alkaline salt; 4 to 20% of binder, preferably polyvinylpyrrolidone; 10 to 50% of soluble diluents, preferably lactose with granulating liquid, preferably selected from an alcohol and/or water; and compressing thus formed granulate into tablet core, such tablet core will be alkaline, having pH above 8, preferably above 9 or 10.

Said optional coating is preferably a film coating and comprises acrylic polymer and/or polyethileneglycols and/or polyvinylpyrrolidone and/or cellulose ethers, and preferably comprises an acidifying agent. Especially presence of polyvinylpyrrolidone allows for Said coating comprising 6-chloro-3,4-dihydro-2H-1,2,4-benzotiadiazine-7-sulfonamide-1,1-dioxide preferably comprises 10 to 40% hydrochlorothiazide and 10 to 40% of substance with suspension stabilizing properties, preferably colloidal silicon dioxide, 20 to 60% of a binder, preferably polyvinylpyrrolidone, 5 to 50% plasticizer and optionally up to 10% acidifying agent by weight of the coating.

Yet another aspect of the invention is a process for manufacturing a pharmaceutical composition characterized by following steps:

preparing first granulate comprising 2-[4-[[4-methyl-6-(1-methylbenzoimidazol-2-yl)-2-propyl-benzoimidazol-1-yl]methyl]phenyl]benzoic acid or its salt characterized in that said first granulate imparts pH above 8 to the 1% by weight to aqueous solution or dispersion thereof; preparing second granulate comprising 6-chloro-3,4-dihydro-2H-1,2,4-benzotiadiazine-7-sulfonamide-1,1-dioxide and polyvinylpyrrolidone; and compressing said first and second granulate together with a carrier into tablet;

preferably wherein said second granulate comprises 10 to 40% hydrochlorothiazide and 10 to 40% of substance with suspension stabilizing properties, preferably colloidal silicon dioxide, 20 to 60% of a binder, preferably polyvinylpyrrolidone, 5 to 50% of plasticizer and optionally up to 10% acidifying agent by weight relative to the weight of said second granulate and more preferably wherein said carrier comprises one or more diluents, binders and lubricants.

DETAILED DESCRIPTION OF THE INVENTION

For bilayer tablets described in WO 03/059327 a special tableting machinery is required. Therefore a process for the manufacturing of a stable combination of first alkaline drug and second drug, which is not stable in alkaline environment, in particular telmisartan and hydrochlorothiazide using conventional equipment is desirable, which would nevertheless overcome the adverse effect on the stability of said second drug, in particular hydrochlorothiazide, caused by alkaline active ingredient (first drug) or inactive ingredients in the pharmaceutical composition.

In developing alternative technologies we observed that in one embodiment the stability of hydrochlorothiazide in a combination formulation with telmisartan can be significantly improved by means of a coated composition comprising telmisartan in at least one unit and hydrochlorothiazide outside said unit, wherein the hydrochlorothiazide could be applied as constituent of a coating, that is a layer applied onto said at least one units, preferably a film coating or a sugar coating.

Alternatively we have also observed that a stable composition of telmisartan and hydrochlorothiazide can be obtained in another embodiment by simple mixing of the telmisartan part of the composition which is in the form of units and a hydrochlorothiazide part of the formulation which is also in the form of units together with the appropriate carrier, following by compression into tablets.

The units mentioned above are assemblies or aggregates of a pharmaceutical active ingredient with inactive ingredients, preferably compacted (e.g. by granulation, extrusion and optionally spheronization) or compressed together, or grind from larger chunks and have diameter from 0.3 to 15 mm, and are preferably selected from granules which include agglomerates, where their diameter is preferably from 0.3 to 1.2 mm, pellets where their diameter is preferably from 0.5 to 2 mm or tablet cores where their diameter is preferably from 2 to 15 mm. It is clear that for the second embodiment, the units will be smaller than for the first, and for the second embodiment are proffered granules or pellets, while for the first tablet cores.

Typical embodiments of the invention are thus: coated tablets, containing tablet core as first unit comprising telmisartan; and coating comprising hydrochlorothiazide onto those tablets; or tablets manufactured by compressing two granulates together with a carrier, where first units are the granules comprising telmisartan and second units are granules comprising hydrochlorothiazide; alternative embodiment are capsules containing those two granulates, alternatively one or both of those units may be replaced by agglomerates, pellets, or small tablets.

Preferably the coated tablets of our invention will be uniform tablets, that is tablets which may be made using conventional tableting equipment in a single step, and the uniformity is characterized in that the units above (e.g. one or more granulates) are substantially evenly distributed throughout the whole tablet.

The stability of the formulation can be additionally improved by a separating coating applied onto telmisartan containing units and/or by incorporating to the hydrochlorothiazide part of the combination formulation one or more acidic component or a combination of acidic components, which are characterized in that their 1% (w/v) aqueous dispersion or solution has a pH<6, preferably pH<5. Optionally, acidic components can also be incorporated in the separating coating.

In accordance with both embodiments we have prepared pharmaceutical compositions comprising telmisartan and hydrochlorothiazide, exposed them to stress stability testing at 60° C. for 14 days and at 40° C. at 75% relative humidity for one month and compared the amount of formed degradation products. We have on one hand followed the amount of all impurities (arising from telmisartan and hydrochlorothiazide) as well as specifically the amount of DSA. Results are presented in following Table:

| Example | Test time and conditions | Total impurities [%] | DSA [%] |
|---------|--------------------------|----------------------|---------|
| 1 | start | 0.19 | 0.06 |
|   | 14 days, 60° C. | 4.05 | 2.99 |
|   | 1 month, 40° C. | 0.92 | 0.81 |
| 2 | start | 0.21 | 0.05 |
|   | 14 days, 60° C. | 1.79 | 1.04 |
|   | 1 month, 40° C. | 0.20 | 0.14 |
| 3 | start | 0.16 | 0.09 |
|   | 14 days, 60° C. | 0.85 | 0.73 |
| 4 | start | 0.18 | 0.11 |
|   | 14 days, 60° C. | 0.35 | 0.28 |
| 5 | start | 0.61 | 0.08 |
|   | 14 days, 60° C. | 0.86 | 0.36 |
| 6 | start | 1.58 | 1.40 |
|   | 14 days, 60° C. | 17.41 | 17.35 |
| 7 | start | 4.50 | 4.40 |
|   | 14 days, 60° C. | 23.88 | 22.97 |

We have generally observed that the stability of hydrochlorothiazide is satisfactorily when providing a separating layer and/or incorporating an acidifying substance into the hydrochlorothiazide containing part of the composition.

The results show that good stability of hydrochlorothiazide is achieved by incorporation of polyvinylpyrrolidone as a binder in units comprising telmisartan and also in the hydrochlorothiazide containing part of the composition.

A good stability is also observed when forming two different granulates, one containing telmisartan and the other hydrochlorothiazide, and compressing them into tablets (Example 2) Any polymer appropriate for solid dispersion (eg. cellulose dervates, acrylates, agar) could be used for hydrochlorothiazide granulate preparation. Optionally acidic excipients such as organic acids, colloidal silicone dioxide and similar could be added to granulate.

In particular the presence of polyvinylpyrrolidone and colloidal silicon dioxide in hydrochlorothiazide containing part of formulation reduces the degradation of hydrochlorothiazide in pharmaceutical composition (Example 3).

Hydrochlorothiazide substance can be additionally stabilized by the presence of an acidic ingredient such as citric acid and/or an intermediate layer (Example 4).

Comparing with Example 5 one sees that all those embodiments provide similar stabilizing effect.

Comparatively the conventional direct compression (Example 6), of the same constituents as in Example 2 resulted in decreased stability of hydrochlorothiazide. Surprisingly the addition of acidic component did not increase stability as seen in Example 7 with same constituents as in Example 1. Those two comparative examples shows that the stability of the composition depends more on the used process than careful choice of the excipients.

In accordance with our invention we are thus able to manufacture a stable composition comprising telmisartan and hydrochlorothiazide by first preparing units, which may be granules, pellets, tablet cores and are in first preferred embodiment tablet cores and in second preferred embodiment granules comprising 1 to 40% preferably 5 to 33%, more preferably 7-20% of telmisartan; 1 to 40% of binder, preferably 4 to 20%, which is preferably selected from polyvinylpyrrolidone, HPC (hydroxypropyl cellulose), LHPC, HPMC (hydroxypropylmethyl cellulose), more preferably polyvinylpyrrolidone; 1 to 75% preferably 10 to 50%, more preferably 20-40% of soluble diluent, which is preferably one or more of saccharides or polyols, such as lactose or sorbitol; and 1 to 20%, preferably 1 to 10% of an alkalizing agent, which is preferably NaOH or meglumine or mixture thereof.

Said units will in 1% (w/v) aqueous suspension or solution have pH above 8, preferably above 9; and wherein the % refer to the weight % of the finished composition.

To those units in one embodiment an optional separating coating is applied comprising any polymer appropriate for conventional film coating (like cellulose ethers, acrylic polymers, polyvinylpyrrolidone, PEG), where said separating coating to about 20%, preferably from 0.1 to about 2% by weight of the finished composition.

Thereto a subsequent layer is applied which comprises 10 to 40% hydrochlorothiazide and 10 to 40% of substance with suspension stabilizing properties, preferably colloidal silicon dioxide; 20 to 60% of suitable binder, preferably polyvinylpyrrolidone; 5 to 50%, preferably 10 to 35% of plasticizer, which may be preferably PEG (polyethyleneglycol), citric acid and its derivates and optionally up to 10% of acidifying agent; and wherein the % refer to the weight % of the coating and the coating constitutes from about 3 to about 33%, preferably around 5 to 15% by weight of the finished composition.

Alternatively in another embodiment said first units comprising telmisartan are combined with second units, and with appropriate carrier.

Those second units are preferably pellets or granules and preferably comprise 2 to 20%, preferably 5-10% of hydrochlorothiazide; 10 to 95%, preferably 50-90%, of soluble diluent as above; 1 to 10% of colloidal silicon dioxide; 2 to 20%, preferably 5-15%, of binder, which is most preferably polyvinylpyrrolidone and optionally up to 10% acidifying agent as above and wherein the % refer to the weight % of said second units;

An appropriate carrier comprises substantially one or more diluents, but also binders and lubricants, which may be cellulose derivatives, preferably microcrystalline cellulose, acrylic polymers, polyvinylpyrrolidone, PEG, magnesium stearate. The weight ratios of said first units, second units and carrier may be 1-10:1-5:1-5., preferably around 2:1.5:1.

The special stabilizing effect of the polyvinylpyrrolidone as a binder is evident and thus our invention is embodied in a pharmaceutical composition comprising hydrochlorothiazide and telmisartan, preferably separated from being in direct contact characterized in that polyvinylpyrrolidone is incorporated into the hydrochlorothiazide containing part of the composition.

The invention is illustrated in more detail by the following non-limiting examples.

Example 1

024T004A

|  |  |  | per coated tbl [mg] | % |  |
|---|---|---|---|---|---|
|  | TABLET CORE |  | 480.00 |  |  |
|  | INTERMEDIATE COATING |  |  |  |  |
| 1(a) | HPMC |  | 19.96 | 81.00% | film forming polymer |
| 2(b) | HYDROXYPROPYL CELLULOSE |  | 0.04 | 18.00% | film forming polymer |
| 3 | PIGMENT |  | 0.04 | 1.00% | pigment |
| 4* | ETHANOL 96% |  | 36.00 |  | solvent |
| 5* | DEMI WATER |  | 4.00 |  | solvent |
|  | mass of inter. layer = |  | 5.00 | 100.00% |  |
|  | COATING WITH HCT |  |  |  |  |
| 1 | HYDROCHLOROTHIAZIDE |  | 12.50 | 35.71% | active pharm. ingredient |
| 2(a) | HPMC |  | 12.00 | 34.29% | film forming polymer |
| 3(b) | HYDROXYPROPYL CELLULOSE |  | 2.50 | 7.14% | film forming polymer |
| 4 | POLYSORBATE 80 V |  | 0.50 | 1.43% | solubilizer |
| 5 | POLYPLASDONE XL |  | 7.45 | 21.29% | disitegrant |
| 6 | PIGMENT RED 30 E172 |  | 0.05 | 0.14% | pigment |
| 7* | ETHANOL 96% |  | 385.56 |  | solvent |
| 8* | DEMI WATER |  | 114.44 |  | solvent |
|  | mass of HCT coating = |  | 35.00 | 100.00% |  |
|  | mass of coated tablet = |  | 520.00 |  |  |

*Not present in tablet
(a)substitution grade 2910
(b)Mw = 80.000

Telmisartan tablet cores prepared by compression of a blend containing per tbl. telmisartan (80 mg), NaOH (6.72 mg), meglumine (24 mg), polyvinylpyrrolidone (24 mg), ludipress (80 mg) [granulate 1 of Example 2], with 237 mg per tbl. of anhydrous lactose and 4 mg per tbl. of magnesium stearate are coated first to produce intermediate coating and subsequently to produce HCT coating by conventional film-coating technology using conventional equipment suitable for film- and/or sugar-coating.

Example 2

201A

|  |  | per tbl [mg] | % in gran. | % per tbl. |  |
|---|---|---|---|---|---|
|  | GRANULATE 1 |  |  |  |  |
| 1 | TELMISARTAN | 80.00 | 37.26% | 15.38% | active pharm. ingredient |
| 2 | NaOH | 6.72 | 3.13% | 1.29% | alkalizing agent |
| 3 | MEGLUMINE | 24.00 | 11.18% | 4.62% | alkalizing agent |
| 4 | POLYVINYLPYRROLIDONE | 24.00 | 11.18% | 4.62% | binder, matrix forming polymer |
| 5 | LUDIPRESS [(1)] | 80.00 | 37.26% | 18.71% | soluble filler |
| 6* | DEMI WATER | 168.00 |  |  | solvent |
| 7* | ETHANOL 96% | 40.00 |  |  | solvent |
|  | GRANULATE 2 |  |  |  |  |
| 1 | HYDROCHLOROTHIAZIDE | 12.50 | 6.68% | 2.31% | active pharm. ingredient |
| 2 | POLYVINYLPYRROLIDONE | 12.50 | 6.68% | 2.31% | inder, atrix forming polymer |
| 3 | LACTOSE, ANHYDROUS | 160.00 | 85.56% | 29.63% | soluble filler |
| 4 | COLLOIDAL $SiO_2$ | 2.00 | 1.07% | 0.37% | emulsion stabilizer, acidifying agent, |
| 5* | ABSOLUTE ETHANOL | 470.00 |  |  | solvent |
| 1 | DRY GRANULATE 1 | 214.72 |  | 39.76% |  |
| 2 | DRY GRANULATE 2 | 187.00 |  | 34.63% |  |
| 3 | CELLULOSE, (Silic. microcrist.) | 130.28 |  | 24.13% | dry filler separating agent |
| 4 | MAGNESIUM STEARATE | 8.00 |  | 1.48% | lubricant |
|  | tablet mass = | 540.00 |  | 100.00% |  |

*Not present in tablet

[(1)] Co-processed excipient made of lactose, polyvinylpyrrolidone, and crospovidone Granulate 1 is prepared by spraying telmisartan dispersion with PVP, NaOH, meglumine on Ludipress particles and granulate 2 by spraying of hydrochlorothiazide dispersion with PVP, colloidal silicone dioxide on lactose particles. Both dry granulates are mixed with silicified MCC and Mg-stearate and compressed into tablets.

pH of Granulate 1 dispersed in approximately 250 ml of water is about 10 (1% aqueous solution). Comparatively pH = 9.75 was measured when tablet made by compressing a granulate consisting: of 80 mg TLS, 6.72 mg NaOH, 24 mg meglumine, 24 mg polyvinylpyrrolidone and 97 mg Ludipress together with 140 mg of Pharmaburst and 140 mg Prosolv and 8 mg Mg stearate, was dissolved in 250 ml water (2% aq. solution relative to whole tablet). Replacing part of Prosolv or Pharmaburst with polyvinylpyrrolidone produced pH = 9.8. Comparatively replacing meglumine with Prosolv or Pharmaburst produced tablets having pH = 8.1 in 2% aqueous dispersion.

Example 3

PL2J006B

|  |  | per coated tbl [mg] |  |  |
|---|---|---|---|---|
|  | CORE of Example 1 | 480.00 |  |  |
|  | COATING WITH HCT |  |  |  |
| 1 | HYDROCHLOROTHIAZIDE | 12.50 | 17.86% | active pharm. ingredient |
| 2 | COLLOIDAL $SiO_2$ | 12.50 | 17.86% | emulsion stabilizer, acidifying agent, film disintegrating agent |
| 3 | CITRIC ACID | 1.26 | 1.80% | acidifying agent |
| 4 | POLYVINYLPYRROLIDONE | 43.70 | 62.42% | film/matrix forming polymer, HCT stabilizer |
| 5 | PIGMENT RED 30 E172 | 0.04 | 0.06% | pigment |
| 6 | ETHANOL 96% | 192.78 |  | solvent |
| 7 | DEMI WATER | 57.22 |  | solvent |
|  | mass of HCT coating = | 50.00 | 100.00% |  |
|  | mass of coated tablet = | 550.00 |  |  |

* Not present in tablet

Telmisartan tablet cores prepared as in example 1 are coated to produce HCT coating by conventional film-coating technology using conventional equipment suitable for film- and/or sugar-coating.

Example 4

PL2J006C

|  | | per coated tbl [mg] | % | |
|---|---|---|---|---|
| | CORE of example 1 | 480.00 | | |
| | INTERMEDIATE COATING | | | |
| 1 | POLYVINYLPYRROLIDONE | 19.96 | 99.80% | film forming polymer |
| 2 | PIGMENT | 0.04 | 0.20% | pigment |
| 3 | ETHANOL 96% | 192.78 | | solvent |
| 4 | DEMI WATER | 57.22 | | solvent |
| | mass of inter. layer = | 20.00 | 100.00% | |
| | COATING WITH HCT | | | |
| 1 | HYDROCHLOROTHIAZIDE | 12.50 | 25.00% | active pharm. ingredient |
| 2 | COLLOIDAL SiO$_2$ | 12.50 | 25.00% | emulsion stabilizer, acidifying agent, film disintegrating agent |
| 3 | CITRIC ACID | 1.26 | 2.52% | acidifying agent |
| 4 | POLYVINYLPYRROLIDONE | 23.70 | 47.40% | film/matrix forming polymer, HCT stabilizer |
| 5 | PIGMENT RED 30 E172 | 0.04 | 0.08% | pigment |
| 6 | ETHANOL 96% | 385.56 | | solvent |
| 7 | DEMI WATER | 114.44 | | solvent |
| | mass of HCT coating = | 50.00 | 100.00% | |
| | mass of coated tablet = | 550.00 | | |

* Not present in tablet
Telmisartan tablet cores prepared as in example 1 are coated first to produce intermediate coating and subsequently to produce HCT coating by conventional film-coating technology using conventional equipment suitable for film- and/or sugar-coating.

Example 5

Bilayer Tablets Corresponding to WO 03/059327

| component | content [mg/tbl] | | |
|---|---|---|---|
| TELMISARTAN | 80.00 | 80.00 | active pharm. ingredient |
| SODIUM HYDROXIDE | 3.36 | 6.72 | pH modifying agent |
| MEGLUMINE | 12.00 | 24.00 | pH modifying agent |
| POLYVINYLPYRROLIDONE | 12.00 | 24.00 | binder, matrix former |
| SORBITOL | 168.64 | 337.28 | soluble filler |
| MAGNESIUM STEARATE | 4.00 | 8.00 | lubricant |
| mass of first blend [mg] | 240.00 | 480.00 | |
| HYDROCHLOROTHIAZIDE | 12.50 | 12.50 | active pharm. ingredient |
| LACTOSE MONOHYDRATE | 112.17 | 112.17 | soluble filler |
| MICROCRYSTALLINE CELLULOSE | 64.00 | 64.00 | filler, diner, disintegrant |
| MAIZE STARCH | 6.00 | 6.00 | filler, inder, disintegrant, lubricant |
| IRON OXIDE | 0.33 | 0.33 | pigment |
| SODIUM STARCH GLYCOLATE | 4.00 | 4.00 | disintegrant |
| MAGNESIUM STEARATE | 1.00 | 1.00 | lubricant |
| mass of second blend [mg] | 200.00 | 200.00 | |

Two separate blends one containing telmisartan and second containing hydrochlorothiazide are compressed into bilayer tablets.

Example 6

Tablets Prepared by Direct Compression

| component | content [mg/tbl] | | |
|---|---|---|---|
| TELMISARTAN | 80.00 | 80.00 | active pharm. ingredient |
| HYDROCHLOROTHIAZIDE | 12.50 | | |
| SODIUM HYDROXIDE | 6.72 | 6.72 | pH modifying agent |
| COLLOIDAL SiO$_2$ | 2.00 | | |
| LACTOSE MONOHYDRATE | 160.00 | | |
| LUDIPRESS | 80.00 | | |
| MEGLUMINE | 24.00 | 24.00 | pH modifying agent |
| POLYVINYLPYRROLIDONE | 36.50 | 24.00 | binder, matrix former |
| SORBITOL | 168.64 | 337.28 | soluble filler |
| CELLULOSE, (Silic. microcrist.) | 130.28 | | |
| MAGNESIUM STEARATE | 8.00 | 8.00 | lubricant |
| mass of blend [mg] | 540.00 | 480.00 | |

Example 7

Tablets Prepared by Direct Compression Including Acidic Component

| component | content [mg/tbl] | | |
|---|---|---|---|
| TELMISARTAN | 40.00 | 80.00 | active pharm. ingredient |
| HYDROCHLOROTHIAZIDE | 12.50 | | |
| BETA LACTOSE | 237.28 | | |
| CITRIC ACID | 1.26 | | |
| HPC | 3.40 | | |
| LUDIPRESS | 80.00 | | |
| MEGLUMINE | 24.00 | | |
| MAGNESIUM STEARATE | 4.00 | | |
| SODIUM HYDROXIDE | 6.72 | 6.72 | pH modifying agent |
| HPMC | 16.05 | | |
| POLYVINYLPYRROLIDONE | 48.00 | | |
| POLYSORBAT 80 V | 0.50 | | |
| POLYPLASDONE XL | 7.45 | | |
| mass of blend [mg] | 521.16 | 480.00 | |

Blends are compressed into tablets.

The degradation products are analyzed by HPLC detected by UV at λ=228 nm using following procedure: 50 μl samples were at 30° C. eluted on Hypersil BDS C18, 5 μm, 250×4.6 mm column at flow rate 1.5 mL/min using following gradient: until 25 min: 90% A—10% B, from 25 min to 45 min 50% A—50% B and after 45 min 20% A—80% B, where A is a solution of KH$_2$PO$_4$/Et$_3$N with pH 3.5, and B is a solution of KH$_2$PO$_4$/Et$_3$N with pH 3.5 and acetonitrile 1:4. All impurities eluted within 25 minutes including DSA represent the total amount of hydrochlorothiazide impurities. Impurities eluted thereafter are assigned to telmisartan. Total impurities presented in Table are sum of impurities of hydrochlorothiazide and telmisartan being calculated as follows:

a) for substance eluted within 25 minutes $$\frac{M_S * A_{V_T} * M * C}{M_v * A_s * D * 400} = \% \text{ of Related Substance}$$

Mv=initial mass of the substance to be tested in mg
Ms=initial mass of the working standard in the reference solution in mg
Av=peak area of the impurity in the chromatogram of the test solution
As=peak area of hydrochlorothiazide substance in the chromatogram of the reference solution
M=average mass of the tablets
D=decelerated content of hydrochlorothiazide in the tablet
C=content of hydrochlorothiazide in the working standard in %
400=dilution factor from reference stock solution to reference solution, b) for substance eluted after 25 minutes relating to telmisartan:

$$\frac{M_s * A_v * M * C}{M_v * A_s * D * 400} = \% \text{ of Related Substance}$$

$M_v$=initial mass of the substance to be tested in mg
$M_s$=initial mass of the telmisartan working standard in the reference solution in mg
Av=peak area of the related substance in the chromatogram of the test solution
M=average mass of tablets
D=decelerated content of telmisartan in the tablet
As=peak area of telmisartab in the chromatogram of the reference solution
C=content of telmisartan in the working standard in %
400=dilution factor from reference stock solution to reference solution.

The invention claimed is:
1. A pharmaceutical composition comprising more than one first unit, selected from the group consisting of granules, pellets, and tablet cores;
   wherein said more than one first unit comprises a first active pharmaceutical ingredient together with pharmaceutically acceptable excipients and
   more than one second unit, selected from the group consisting of granules, pellets and tablet cores, wherein said more than one second unit comprises a second active pharmaceutical ingredient, together with pharmaceutically acceptable excipients, wherein said more than one first unit and more than one second unit are combined together with a suitable carrier and compressed into a tablet where said units are substantially evenly distributed throughout the tablet;
   wherein the second active pharmaceutical ingredient is 6-chloro-3,4-dihydro-2H-1,2,4-benzotiadiazine-7-sulfonamide-1,1-dioxide and the more than one first unit alone imparts a pH above 8 to a 1% by weight aqueous solution or dispersion of the more than one first unit, where said more than one first unit comprises 2-[4-[[4-methyl-6-(1-methylbenzoimidazol-2-yl)-2-propyl-benzoimidazol-1-yl]methyl]phenyl] benzoic acid or a salt thereof as the first active pharmaceutical ingredient, and wherein the more than one second units further comprise an acidifying agent and wherein the more than one second unit alone imparts a pH below 6 to a 1% by weight aqueous solution or dispersion of the more than one second unit.

2. A pharmaceutical composition according to claim 1 comprising more than one first unit, selected from the group consisting of granules, pellets and tablet cores comprising 2[4[[4-methyl-6-(1-methylbenzoimidazol-2-yl)-2-propyl-benzoimidazol-1-yl]methyl]phenyl] benzoic acid or a salt thereof, with optional coating applied to said more than one first unit, wherein said coating comprises a polymer appropriate for conventional film coating; and more than one second unit, selected from the group consisting of granules and pellets, comprising 6-chloro-3,4-dihydro-2H-1,2,4-benzotiadiazine-7-sulfonamide-1,1-dioxide, wherein said more than one first unit and more than one second unit are together with a suitable carrier compressed into a pharmaceutical composition.

3. A pharmaceutical composition according to claim 1, wherein the more than one second units comprise 3 to 15% 6-chloro-3,4-dihydro-2H-1,2,4-benzotiadiazine-7-sulfonamide-1,1-dioxide, 10 to 95% of one or more soluble diluents, 1 to 10% of substance with suspension stabilizing properties, 5 to 15% of binder, and optionally up to 10% of an acidifying agent by weight relative to the weight of said second units.

4. The pharmaceutical composition according to claim 3, wherein the more than one first units comprise 1 to 50% of 2-[4-[[-methylbenzoimidazol-2-yl)-2-propyl-benzoimidazol-1-yl]methyl]phenyl] benzoic acid or a salt thereof; 1 to 50% binder, 1 to 80% soluble diluent, and 1 to 12% alkalizing agent by weight relative to the weight of the first units.

5. The pharmaceutical composition of claim 3, wherein the soluble diluents are lactose, the substance with suspension stabilizing properties is colloidal silicon dioxide, the binder is polyvinylpyrrolidone and the optional acidifying agent is citric acid.

6. A process for manufacturing a pharmaceutical composition comprising manufacturing more than one first unit comprising 2-[4-[[4-methyl-6-(1-methylbenzoimidazol-2-yl)-2-propyl-benzoimidazol-1-yl]methyl]phenyl] benzoic acid or its salt, wherein the more than one first unit alone imparts a pH above 8 to a 1% by weight aqueous solution or dispersion of the more than one first unit;

applying onto the more than one first unit an optional separating coating; and manufacturing more than one second unit comprising 6-chloro-3,4-dihydro-2H-1,2,4-benzotiadizine-7-sulfonamide-1,1-dioxide and an acidifying agent, wherein the more than one second unit alone imparts a pH below 6 to a 1% by weight aqueous solution or dispersion of the more than one second unit; and combining the more than one first unit and more than one second unit and compressing them together with a suitable carrier into a tablet where said units are substantially evenly distributed throughout the tablet.

7. A process for manufacturing a tablet comprising the steps of:

a) preparing a first granulate comprising 2-[4-[[4-methyl-6-(1-methylbenzoimidazol-2-yl)-2-propyl-benzoimidazol-1-yl]methyl]phenyl] benzoic acid or its salt, characterized in that said first granulate imparts a pH above 8 to a 1% by weight of an aqueous solution or dispersion thereof;

b) preparing a second granulate comprising 6-chloro-3,4-dihydro-2H-1,2,4-benzotiadiazine-7-sulfonamide-1,1-dioxide and polyvinylpyrrolidone and an acidifying agent, wherein the second granulate imparts a pH below 6 to a 1% by weight aqueous solution or dispersion of the second granulate; and c) compressing said first and second granulate together with a carrier into a tablet wherein the first and second granulates are substantially evenly distributed throughout the tablet.

* * * * *